(12) United States Patent
Cooney et al.

(10) Patent No.: US 8,574,923 B2
(45) Date of Patent: Nov. 5, 2013

(54) SAMPLE PREPARATION DEVICE

(71) Applicant: Akonni Biosystem, Inc., Frederick, MD (US)

(72) Inventors: Christopher G. Cooney, Severn, MD (US); Phillip Belgrader, Livermore, CA (US)

(73) Assignee: Akonni Biosystems, Inc., Frederick, MD (US)

( * ) Notice: Subject to any disclaimer, the term of this patent is extended or adjusted under 35 U.S.C. 154(b) by 0 days.

(21) Appl. No.: 13/682,551

(22) Filed: Nov. 20, 2012

(65) Prior Publication Data

US 2013/0078619 A1 Mar. 28, 2013

Related U.S. Application Data

(60) Division of application No. 12/213,942, filed on Jun. 26, 2008, which is a continuation-in-part of application No. 11/933,113, filed on Oct. 31, 2007, now Pat. No. 7,759,112.

(51) Int. Cl.
    *G01N 1/34* (2006.01)
(52) U.S. Cl.
    USPC ............ 436/178; 436/174; 436/177; 436/161
(58) Field of Classification Search
    USPC ........... 436/161, 178; 422/524, 527, 534, 535
    See application file for complete search history.

(56) References Cited

U.S. PATENT DOCUMENTS

| | | | |
|---|---|---|---|
| 4,475,821 A | 10/1984 | Koch et al. | |
| 4,765,818 A | 8/1988 | Che et al. | |
| 4,810,674 A | 3/1989 | Che et al. | |
| 4,999,164 A | 3/1991 | Puchinger et al. | |
| 5,496,523 A | 3/1996 | Gazit et al. | |
| 5,833,927 A | 11/1998 | Raybuck et al. | |
| 5,876,918 A | 3/1999 | Wainwright et al. | |
| 6,048,457 A | 4/2000 | Kopaciewicz et al. | |
| 6,074,827 A | 6/2000 | Nelson | |
| 6,084,091 A | 7/2000 | Muller | |
| 6,100,084 A | 8/2000 | Miles et al. | |

(Continued)

FOREIGN PATENT DOCUMENTS

| | | |
|---|---|---|
| WO | 00/021973 | 4/2000 |
| WO | WO 2007/136715 | * 11/2007 |
| WO | PCT/US08/056482 | 3/2008 |
| WO | PCT/US08/066159 | 6/2008 |

OTHER PUBLICATIONS

Written Opinion and Search Report dated Aug. 25, 2008.
Written Opinion dated Jan. 9, 2009.

(Continued)

*Primary Examiner* — Krishnan S Menon
*Assistant Examiner* — Dwan A Gerido
(74) *Attorney, Agent, or Firm* — Michael Ye; Andrews Kurth LLP (57) ABSTRACT

A sample preparation device is disclosed. The sample preparation device includes a housing defining a passage way between a first opening and a second opening; and a sample filter occupying a section of said passage way. The sample filter contains a monolith adsorbent that specifically binds to nucleic acids. Also disclosed are sample filters containing glass frit is coated with an capture agent that binds specifically to an analyte of interest, sample filters containing a hydrophilic matrix with impregnated chemicals that lyses cell membranes, a cartridge base and an integrated sample preparation cartridge.

17 Claims, 8 Drawing Sheets

(56) References Cited

U.S. PATENT DOCUMENTS

| | | |
|---|---|---|
| 6,200,474 B1 | 3/2001 | Kopaciewicz et al. |
| 6,268,148 B1 | 7/2001 | Barany et al. |
| 6,274,371 B1 | 8/2001 | Colpan |
| 6,337,214 B1 | 1/2002 | Chen |
| 6,391,541 B1 | 5/2002 | Peterson et al. |
| 6,431,476 B1 | 8/2002 | Taylor et al. |
| 6,537,502 B1 | 3/2003 | Shukla et al. |
| 6,699,713 B2 | 3/2004 | Benett et al. |
| 6,881,541 B2 | 4/2005 | Peterson et al. |
| 6,958,392 B2 | 10/2005 | Fomovskaia |
| 6,987,018 B2 | 1/2006 | Taylor et al. |
| 7,097,980 B2 | 8/2006 | Barany et al. |
| 7,157,232 B2 | 1/2007 | Miles et al. |
| 7,541,166 B2 | 6/2009 | Belgrader et al. |
| 2003/0194706 A1* | 10/2003 | Brevnov ............... 435/6 |
| 2004/0054160 A1 | 3/2004 | Pal |
| 2004/0122222 A1 | 6/2004 | Sakurai et al. |
| 2005/0092685 A1 | 5/2005 | Hilborst et al. |
| 2006/0124551 A1* | 6/2006 | Gjerde et al. ............ 210/656 |
| 2006/0160064 A1 | 7/2006 | Carbonnel |
| 2006/0177352 A1 | 8/2006 | Ziegmann et al. |
| 2008/0146789 A1 | 6/2008 | Braman et al. |

OTHER PUBLICATIONS

Search Report dated Jan. 22, 2009.
Niederkofler, et al., "Novel Mass Spectrometric Immunassays for the Rapid Structural Characterization of Plasma Apolipoproteins", Journal of Lipid Research, vol. 44, 2003.
Chandler, et al., Renewable Microcolumns for Solid-Phase Nucleic Acid Separations and Analysis from Environ. Samples:, Trends in Analytical Chemistry, vol. 19, pp. 314-321, 2000.
Whatman Catalog webversion, Mar. 31, 2010, pp. 1 and 2.

* cited by examiner

WORK SEQUENCE

| SEQUENCES/STEPS | DEVICE NAME | FORMAT | PARAMETERS |
|---|---|---|---|
| ⊟ FRIT TIP SAMPLE TOGGL | | | |
| ⊞ AIR BUBBLE | | | |
| FRIT TIP WAS 18 P | 18-PORT | PORT # | 10 |
| MILLIGAT PUMP AS | MILLIGAT PUMP SYSTEM | VOLUME (μL), FLOW RATE(μL/s),HOLD ALL (0/1) | 1000,30,1 |
| WAIT | | TIME(s) | 3 |
| MILLIGAT PUMP DIS | MILLIGAT PUMP SYSTEM | VOLUME (μL), FLOW RATE(μL/s),HOLD ALL (0/1) | 1000,30,1 |
| MILLIGAT PUMP AS | MILLIGAT PUMP SYSTEM | VOLUME (μL), FLOW RATE(μL/s),HOLD ALL (0/1) | 1000,30,1 |
| WAIT | | TIME(s) | 3 |
| MILLIGAT PUMP DIS | MILLIGAT PUMP SYSTEM | VOLUME (μL), FLOW RATE(μL/s),HOLD ALL (0/1) | 1000,30,1 |
| MILLIGAT PUMP AS | MILLIGAT PUMP SYSTEM | VOLUME (μL), FLOW RATE(μL/s),HOLD ALL (0/1) | 1000,30,1 |
| WAIT | | TIME(s) | 3 |
| MILLIGAT PUMP DIS | MILLIGAT PUMP SYSTEM | VOLUME (μL), FLOW RATE(μL/s),HOLD ALL (0/1) | 1000,30,1 |
| MILLIGAT PUMP AS | MILLIGAT PUMP SYSTEM | VOLUME (μL), FLOW RATE(μL/s),HOLD ALL (0/1) | 1100,30,1 |
| ⊞ SELECT WASTE | | | |
| MILLIGAT PUMP DIS | MILLIGAT PUMP SYSTEM | VOLUME (μL), FLOW RATE(μL/s),HOLD ALL (0/1) | 1030,30,1 |
| FRIT TIP WAS 18 P | 18-PORT | PORT # | 10 |
| MILLIGAT PUMP AS | MILLIGAT PUMP SYSTEM | VOLUME (μL), FLOW RATE(μL/s),HOLD ALL (0/1) | 600,40,1 |
| ⊞ SELECT WASTE | | | |
| ⊞ MILLIGAT PUMP DIS | MILLIGAT PUMP SYSTEM | VOLUME (μL), FLOW RATE(μL/s),HOLD ALL (0/1) | 700,30,1 |
| ⊞ FLUSH TO WASTE | | | |

FIG. 8

SAMPLE PREPARATION DEVICE

CROSS-REFERENCE TO RELATED APPLICATIONS

This application is a divisional of U.S. patent application Ser. No. 12/213,942 filed Jun. 26, 2008, which is a continuation-in-part of U.S. patent application Ser. No. 11/933,113 filed Oct. 31, 2007, now U.S. Pat. No. 7,759,112. All of the aforementioned applications are incorporated herein by reference in their entirety.

FIELD

The technical field is sample preparation devices in the biochemical art and, in particular, sample preparation devices using a porous monolith filter for sample filtration, separation and purification.

BACKGROUND

The presence of salts, detergents and other contaminants in a sample can be deleterious to the biochemical analysis of the sample. Many sample preparation devices have been developed in the biochemical art to remove solvent, solute and other molecules/materials from a liquid sample that contains the analyte of interest.

For example, U.S. Pat. Nos. 6,048,457 and 6,200,474 describes pipette tips with chromatography media in them for the purification of proteins and peptides. The chromatography media typically consists of functionalized glass beads with C4, C18, or a strong cationic resin such as polysulfone, polyethersulfone, polytetrafluoroethylene, cellulose acetate, polystyrene, polystyrene/acrylonitrile copolymer and PVDF. U.S. Pat. No. 6,537,502 also describes a sample purification pipette tip having a solid matrix coating on the interior surface of the pipette tip for sample separation and purification. The solid matrix is composed of a polymeric substance such as polytetrafluoroethylene, polysulfone, polyethersulfone, polystyrene, polystyrene/acrylonitrile copolymer, and polyvinylidene fluoride.

There still exists a need, however, for sample preparation devices that are easy to use and can be manufactured at low cost.

SUMMARY

A sample preparation device is disclosed. The sample preparation device includes a housing defining a passage way between a first opening and a second opening; and a sample filter occupying a section of said passage way. The sample filter contains a monolith adsorbent that specifically binds to nucleic acids. Also disclosed are sample filters containing a glass frit, coated with a capture agent that binds specifically to an analyte of interest, and sample filters containing a hydrophilic matrix with impregnated chemicals that lyse cell membranes.

Also disclosed is an integrated sample preparation cartridge. The integrated sample preparation cartridge includes a sample preparation device and a cartridge base. The sample preparation device includes a housing defining a passage way between a first opening and a second opening, and a sample filter occupying a section of the passage way, the sample filter includes an adsorbent that specifically binds to an analyte of interest. The cartridge base includes a first port configured to interface with the sample preparation device, a second port configured to interface with a liquid delivery device, and a first channel connecting the first port to the second port.

Also disclosed is a sample purification system. The sample purification system includes a sample preparation device, a cartridge base and a liquid delivery device.

Also disclosed is a method for purifying an analyte from a sample. The method includes passing a sample through a sample preparation device comprising a housing defining a passage way between a first opening and a second opening, and a filter occupying a section of the passage way, wherein the sample filter comprising a material that specifically binds to said analyte and the sample passes through the sample filter while passing through the sample preparation device; and eluting analyte bound to the sample filter with an eluting solution, wherein the sample and the eluting solution enter and exit the housing through the same opening.

DESCRIPTION OF THE DRAWINGS

The detailed description will refer to the following drawings, wherein like numerals refer to like elements, and wherein:

FIG. 3 shows the real-time PCR analysis of *Bacillus anthracis* nucleic acids purified from a blood sample. Controls include unprocessed *Bacillus anthracis* suspended in water at a concentration of $10^4$ cfu/ml and NTC (no template control).

FIG. 4 shows the real-time PCR analysis of *Streptococcus pyogenes* nucleic acids purified from samples at various *Streptococcus pyogenes* concentrations. Controls are unprocessed sample of *Streptococcus pyogenes* suspended in water at a concentration of $10^4$ cfu/ml and NTC (no template control).

FIG. 5 shows the real-time PCR analysis of *Bacillus anthracis* nucleic acids purified from a nasopharyngeal sample. Controls are unprocessed *Bacillus anthracis* suspended in water at a concentration of $10^4$ cfu/ml FIG. 6 shows the real-time PCR analysis of Venezuela Equine Encephalitis virus nucleic acids purified from a blood sample. Controls are unprocessed Venezuela Equine Encephalitis virus suspended in water at a concentration of $10^4$ pfu/ml and NTC (no template control). All samples are tested in duplicates.

FIG. 7 is a screen shot showing the Sample Toggle screen of the Flow Pro Fluidic Handling System FIG. 8 is a screen shot showing the real time PCR result screen of a Flow Pro Fluidic Handling System (Global FIA, Fox Island, Wash.). Controls are unprocessed *Yersinia pestis* suspended in water at a concentration of $10^4$ cfu/ml and NTC (no template control).

DETAILED DESCRIPTION

This description is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "front," "back," "up," "down," "top" and "bottom," as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected" and "attached," refer to a relationship wherein structures are secured or attached to one another either directly or indirectly through intervening structures, as well as both movable or rigid attachments or relationships, unless expressly described otherwise.

In describing embodiments of the present invention, specific terminology is employed for the sake of clarity. However, the invention is not intended to be limited to the specific terminology so selected. It is to be understood that each specific element includes all technical equivalents which operate in a similar manner to accomplish a similar purpose.

One aspect of the present invention relates to a sample preparation device. In one embodiment, the sample preparation device includes a housing that defines a sample passage way between two openings, and a filter structure embedded in a section of the passage way. The filter structure includes a monolith adsorbent that specifically binds to nucleic acids.

The term "monolith adsorbent" or "monolithic adsorbent material," as used in the embodiments described hereinafter, refers to a porous, three-dimensional adsorbent material having a continuous interconnected pore structure in a single piece. A monolith is prepared, for example, by casting, sintering or polymerizing precursors into a mold of a desired shape. The term "monolith adsorbent" or "monolithic adsorbent material" is meant to be distinguished from a collection of individual adsorbent particles packed into a bed formation or embedded into a porous matrix, in which the end product comprises individual adsorbent particles. The term "monolith adsorbent" or "monolithic adsorbent material" is also meant to be distinguished from a collection of adsorbent fibers or fibers coated with an adsorbent, such as filter papers or filter papers coated with an adsorbent.

The term "specifically bind to" or "specific binding," as used in the embodiments described hereinafter, refers to the binding of the adsorbent to an analyte (e.g., nucleic acids) with a specificity that is sufficient to differentiate the analyte from other components or contaminants of a sample. In one embodiment, the dissociation constant of the adsorbent/ligand complex is less than about $1 \times 10^{-6}$ M. A person of ordinary skill in the art understands that stringency of the binding and elution of the analyte to the adsorbent can be controlled by binding and elution buffer formulations. For example, elution stringencies for nucleic acids can be controlled by salt concentrations using KCl or NaCl. Nucleic acids, with their higher negative charge, are more resistant to elution than proteins. Temperature, pH, and mild detergent are other treatments that could be used for selective binding and elution. Thermal consistency of the binding and elution may be maintained with a heat block or a water bath. The manipulation of the binding buffer is preferable since the impact of the modified elution buffer on the downstream analyzer would need to be evaluated.

The term "nucleic acid," as used in the embodiments described hereinafter, refers to individual nucleic acids and polymeric chains of nucleic acids, including DNA and RNA, whether naturally occurring or artificially synthesized (including analogs thereof), or modifications thereof, especially those modifications known to occur in nature, having any length. Examples of nucleic acid lengths that are in accord with the present invention include, without limitation, lengths suitable for PCR products (e.g., about 50 to 700 base pairs (bp)) and human genomic DNA (e.g., on an order from about kilobase pairs (Kb) to gigabase pairs (Gb)). Thus, it will be appreciated that the term "nucleic acid" encompasses single nucleic acids as well as stretches of nucleotides, nucleosides, natural or artificial, and combinations thereof, in small fragments, e.g., expressed sequence tags or genetic fragments, as well as larger chains as exemplified by genomic material including individual genes and even whole chromosomes.

Figure 1A:
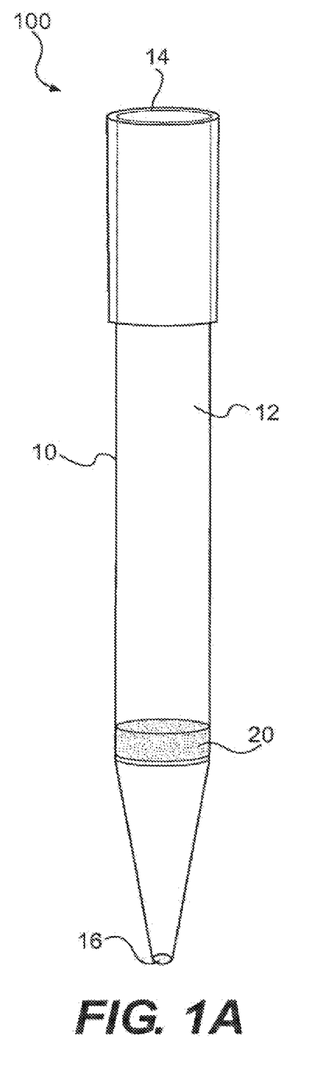
FIGS. 1A-1D are schematics of various embodiments of a sample preparation device.

Referring now to FIG. 1A, an embodiment of the sample preparation device 100 includes a housing 10 and a sample filter 20. The housing 10 defines a sample passage way 12 between a first opening 14 and a second opening 16. The shape and size of the housing 10 are not particularly limited. The preferred housing configuration is substantially cylindrical so that the flow vectors during operation are substantially straight, thereby minimizing or avoiding dilutional washing that might occur with non-cylindrical configurations. In the embodiments shown in FIGS. 1A-1D, the housing 10 has a pipette tip geometry, i.e., the first opening 14 has a diameter that is greater than the diameter of said second opening 16, and the first opening 14 is dimensioned to fit Onto the tip of a pipettor. The sample filter 20 is placed in the close proximity of the second opening 16 so that samples are filtered immediately after being taken into the housing 10 through the second opening 16. In one embodiment, the sample filter 20 is contiguous with the second opening 16. In another embodiment, the sample filter 20 is separated from the second opening 16 by a distance of 1-20 mm. In another embodiment, the housing 10 has a column geometry.

In one embodiment, the housing 10 has a volume of about 0.1 µl to about 10 ml. In another embodiment, the housing 10 has a volume of about 5 µl to about 5 ml. Suitable materials for the housing 10 are not particularly limited, and include plastics (such as polyethylene, polypropylene, and polystyrene), glass and stainless steel.

The sample filter 20 can be made of any porous monolithic material that binds specifically to nucleic acids. The porosity of the porous monolithic material is application dependent. In general, the porous monolithic material should have a porosity that allows for a desired sample flow rate for a particular application.

In one embodiment, the sample filter 20 is made of a finely porous glass frit through which a liquid sample may pass. Porous glass frits, which are sintered glass that begins with crushing beads in a hot press to form a single monolithic structure, are excellent substrates for purifying nucleic acids. The uniform structure of the frit provides predictable liquid flow inside the frit and allows the eluent to have similar fluid dynamics as the sample flow. The predictable liquid flow also leads to a higher recovery during the elution process.

Exemplary glass frit pore sizes suitable for use with the present invention, including the various embodiments described herein, are between about 2 microns and about 220 microns. In one embodiment, the glass frit has a pore size between about 2 microns and about 100 microns. In another embodiment, the glass frit has a pore size between about 40 microns and about 75 microns. In another embodiment, the glass frit has a pore size between about 150 microns and about 200 microns. In yet another embodiment, the glass frit has a pore size between about 2 microns and about 20 microns. For applications involving purification of microbial DNA, a glass frit size of between about 10 microns and about 15 microns is suitable.

In one embodiment, the glass frit has a thickness between about 1 mm and about 20 mm. In another embodiment, the glass frit has a thickness between about 2 mm and about 5 mm. In yet another embodiment, the glass frit has a thickness between about 2 mm and about 3 mm.

In another embodiment, the glass frit is chemically treated to functionalize its surface. For example, the glass frits may be derivatized with aminosilanes or treated with the ChargeSwitch® technology (Invitrogen, Carlsbad, Calif.) to create positive charges for better adsorption of the negatively charged nucleic acids.

While the glass frit is a good adsorbent for nucleic acids, a skilled artisan would recognize that the glass frit may also be used to absorb other types of molecules. For example, the glass frit may be coated with antibodies to extract other ligand of interest from the sample. In one embodiment, the glass frit is derivatized in polymethylmethacrylate (PMMA) and cyclo-olefin-copolymer (COC) with antibodies as capture moieties for microbes and toxin. The term "antibody", as used herein, is used in the broadest possible sense and may include but is not limited to an antibody, a recombinant antibody, a genetically engineered antibody, a chimeric antibody, a monospecific antibody, a bispecific antibody, a multispecific antibody, a chimeric antibody, a heteroantibody, a monoclonal antibody, a polyclonal antibody, a camelized antibody, a deimmunized antibody, and an anti-idiotypic antibody. The term "antibody" may also include but is not limited to an antibody fragment such as at least a portion of an intact antibody, for instance, the antigen binding variable region. Examples of antibody fragments include Fv, Fab, Fab', F(ab'), F(ab')$_2$, Fv fragment, diabody, linear antibody, single-chain antibody molecule, multispecific antibody, and/or other antigen binding sequences of an antibody. In another embodiment, the glass frit is coated with lectins, which bind to carbohydrates found in bacteria coats and can be used to capture bacteria in a sample.

In another embodiment, the sample filter 20 is made of a porous glass monolith, a porous glass-ceramic, or porous monolithic polymers. Porous glass monolith may be produced using the sol-gel methods described in U.S. Pat. Nos. 4,810,674 and 4,765,818, which are hereby incorporated by reference. Porous glass-ceramic may be produced by controlled crystallization of a porous glass monolith.

Porous monolithic polymers are a new category of materials developed during the last decade. In contrast to polymers composed of very small beads, a monolith is a single, continuous piece of a polymer prepared using a simple molding process. In one embodiment, the housing 10 serves as the mold for the porous monolithic polymers. Briefly, a section of the passage way 12 of the housing 10 is filled with a liquid mixture of monomers and porogens. Next, a mask that is opaque to ultraviolet light is placed over the filled section. The mask has a small slit that exposes a small portion of the filled section. Finally, the monomers/porogens mixture in the filled section is irradiated with ultraviolet light through the tiny opening on the mask. The UV irradiation triggers a polymerization process that produces a solid but porous monolithic material in the filled section of the passage way 12.

In yet another embodiment, the sample filter 20 is made of a hydrophilic matrix with impregnated chemicals that lyses cell membranes, denaturing proteins, and traps nucleic acids. In one embodiment, the hydrophilic matrix is FTA Paper® (Whatman, Florham Park, N.J.). Biological samples are applied to the FTA® paper and cells contained in the sample are lysed on the paper. The paper is washed to remove any non-DNA material (the DNA remains entangled within the paper). The DNA is then eluted for subsequent analysis.

The sample filter 20 is shaped to fit tightly into the passage way 12 to prevent the sample from channeling or bypassing the sample filter 20 during operation. In one embodiment, the filter 20 is fitted into the passage way 12 through mechanical means such as crimping, press fitting, and heat shrinking the housing 10 or a portion thereof. In another embodiment, the filter 20 is attached to the interior of passage way 12 through an adhesive. In yet another embodiment, the side of the frit is tapered to the contour of the passage way 12. In the embodiments shown in FIGS. 1A-1D, the housing 10 has the shape of a frustoconical pipette tip with the first opening 14 dimensioned to fit on the end of a liquid delivery system, such as a manual pipettor or an electronic pipetting device. Samples are taken up though the second opening 16, passed through the sample filter 20 and then retained in the section of the housing 10 that is above the sample filter 20. In one embodiment, the liquid delivery system is an electronic pipetting device, such as an electronic pipettor or a robotic pipetting station.

Figure 1B:
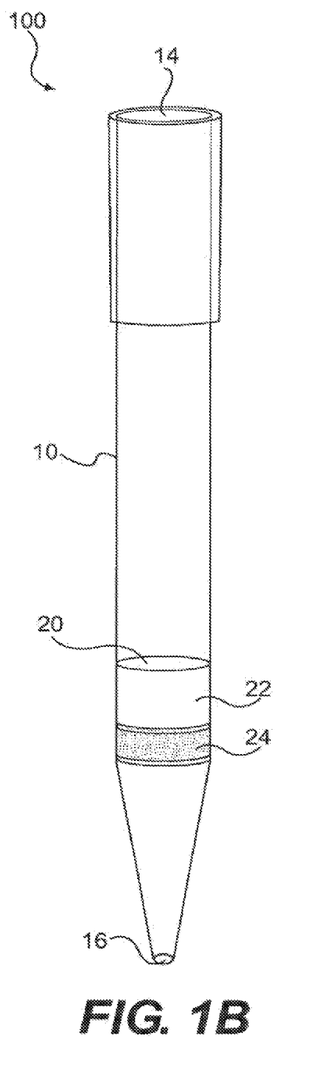
Figure 1C:
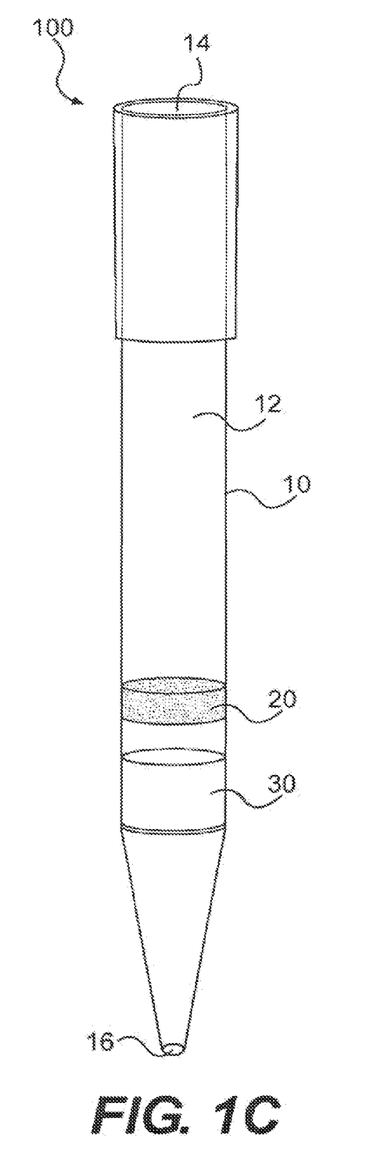
Figure 1D:
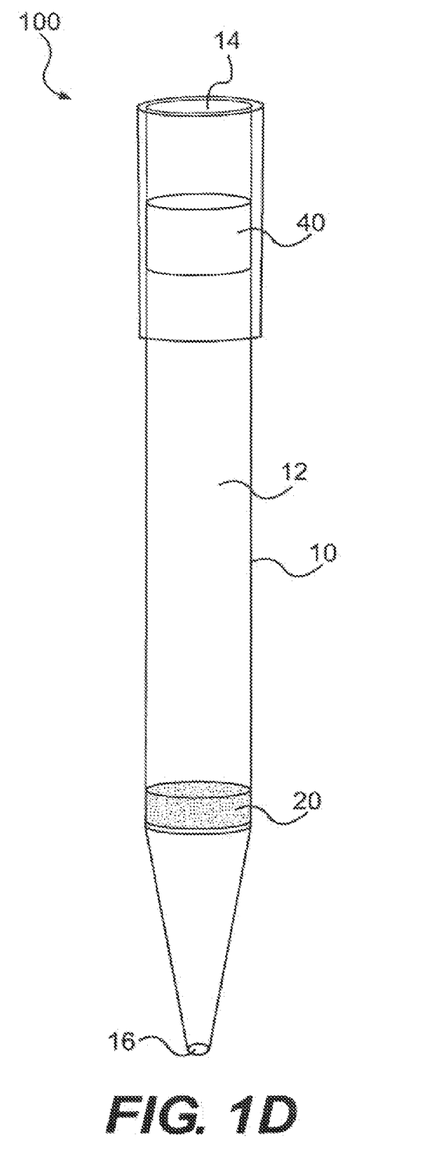

In one embodiment, the sample filter 20 includes at least two sections, a first section 22 that binds specifically to nucleic acids and a second section 24 that specifically binds to another analyte of interest, such as proteins (FIG. 1B). In another embodiment, the housing 10 contains a pre-filter 30 placed between the second opening 16 and the sample filter 20 (FIG. 1C). The pre-filter 30 has a pore size that is larger than the pore size of the sample filter 20 and does not bind specifically to nucleic acids. In yet another embodiment, the housing contains an aerosol filter 40 in the proximity of the first opening 14 to prevent contamination from the pumping device (FIG. 1D).

In another embodiment, the housing 10 further contains a plurality of mechanical lysing beads, such as glass beads, in the space between the sample filter 20 and the aerosol filter 40. The mechanical lysing beads are used to disrupt the cells and release the nucleic acid by vortexing the entire sample preparation device 100. In this embodiment, the second opening 16 may be covered with a cap during vortexing to prevent the liquid from escaping from the second opening 16.

Figure 2A:
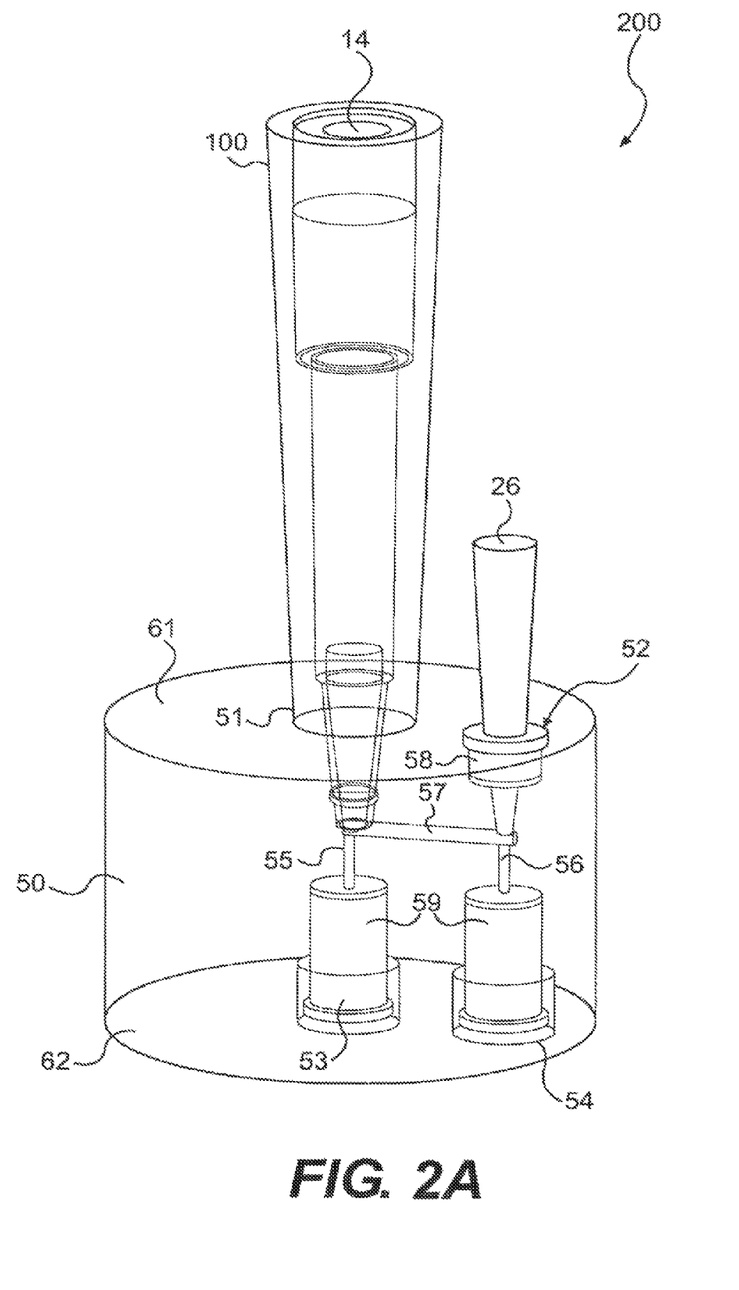
FIG. 2A-2C are schematics of the three-dimensional view (FIG. 2A), the top view (FIG. 2B) and the bottom view (FIG. 2C) of an embodiment of an integrated sample preparation device.
Figure 2B:
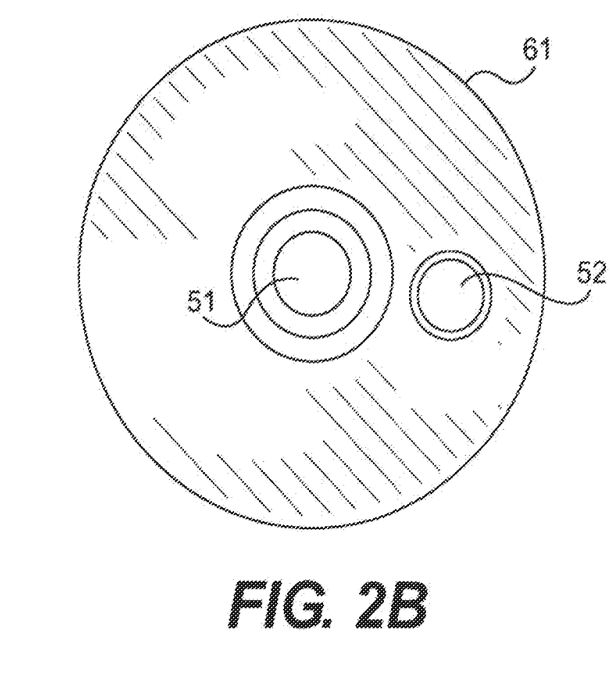
Figure 2C:
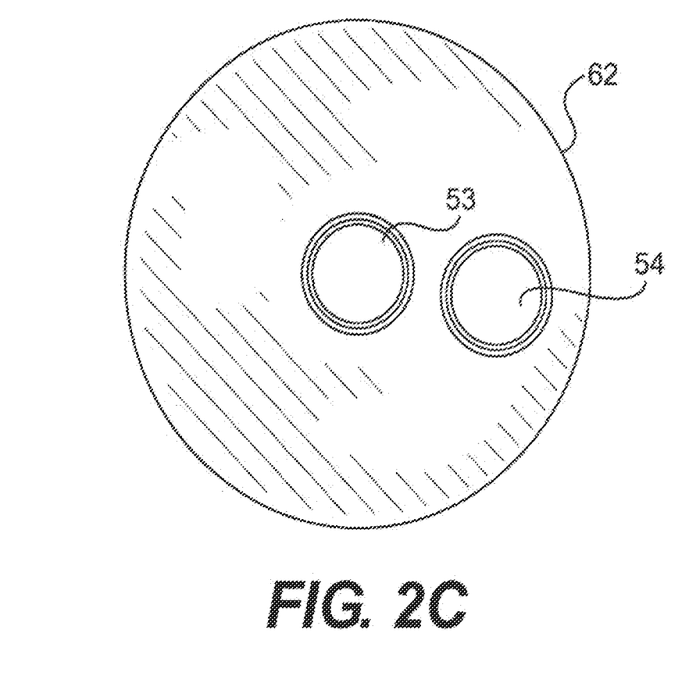
Figure 3:
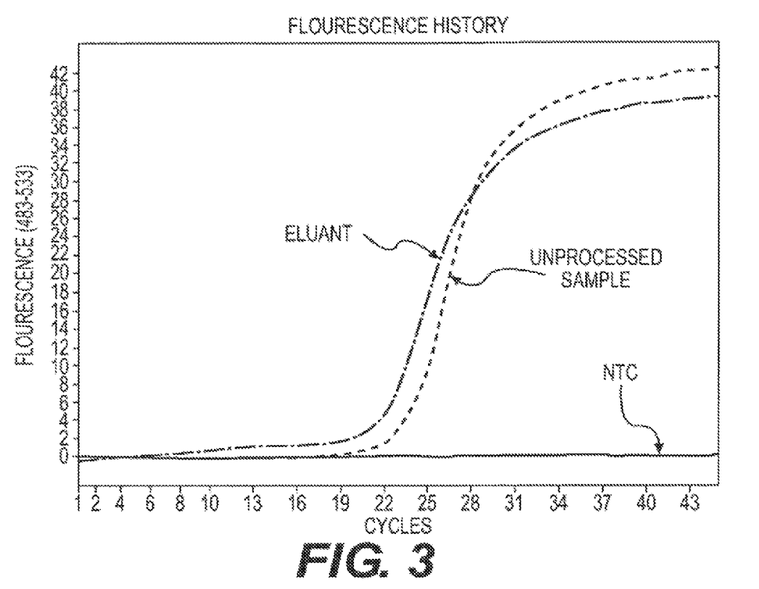
Figure 4:
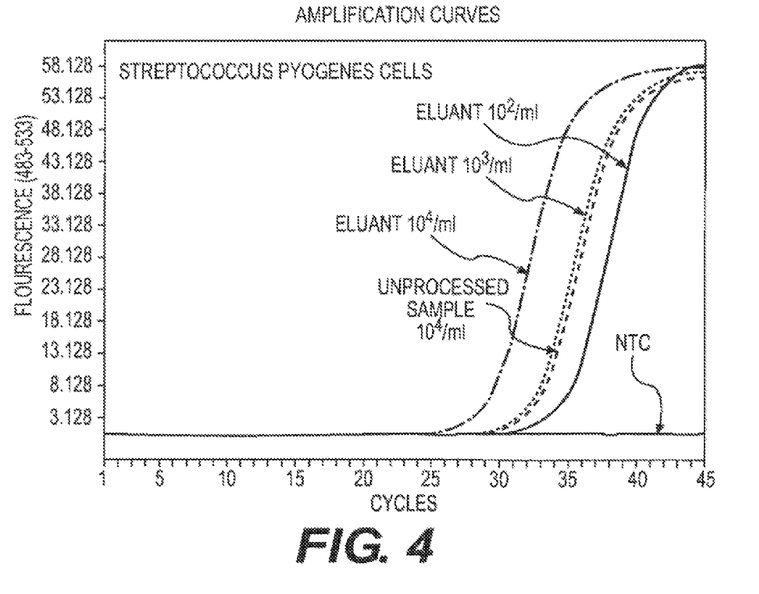

Another aspect of the present invention relates to an integrated sample preparation cartridge. Referring now to FIGS. 2A-2C, an embodiment 200 of the integrated sample preparation cartridge includes a base 50 and the sample preparation device 100. The base 50 contains a first sample port 51 and a second sample port 52 on the top surface 61, a third sample port 53 and a fourth sample port 54 at the bottom surface 62, a first channel 55 connecting the first sample port 51 to the third sample port 53, a second channel 56 connecting the second sample port 52 to the fourth sample port 54, and a third channel 57 connecting the first channel 55 and the second channel 56.

The first sample port 51 is configured to receive the sample preparation device 100, so that the sample preparation device 100, whether in a column configuration or pipette tip configuration, can be easily inserted into the first sample port 51 and form a liquid-tight seal with the base 50.

Once attached to the first sample port 51, the sample preparation device 100 maintains a vertical position. A sample may be loaded onto the sample preparation device 100 from either the first opening 14 (i.e., going down the sample passage way 12) or the second opening 16 (i.e., going up the sample passage way 12). Alternatively, the sample preparation device 100 may be attached to the first sample port 51 with a pre-loaded sample.

The second sample port 52 can also be used to introduce a liquid into the integrated sample preparation cartridge 200 or to take out a liquid from the integrated sample preparation cartridge 200. The second sample port 52 is configured to receive the tip 26 of a liquid delivering device, such as a pipettor or a robotic pipetting station. In one embodiment, the second sample port 52 is a self-sealing inlet containing a seal 58 that can be punctured by a pipette tip and seals after the removal of the tip. Such a self-sealing entry port for a pipette allows easy introduction of the sample without the risk of opening caps, which are often a cause of contamination. In one embodiment, the seal 58 is a Multisip™ split septum plug from Abgene (Epsom, UK). In another embodiment, the seal 58 is a port valve, such as the Duckbill valves and dome valves from Minivalve International (Yellow Springs, Ohio). In another embodiment, the first sample port 51 also contains a self-sealing device, such as a dome valve or a septum, that is receptive to the sample preparation device 100.

In another embodiment, either the first sample port 51 or the second sample port 52 or both ports can be sealed with a screw cap or a press fit cap to allow the introduction and removal of samples. The ports can also be sealed with a tape seal to prevent leaking during the automation process.

The first channel 55, the second channel 56 and the third channel 57 connect the first sample port 51 to the second sample port 52 so that the nucleic acid purification process can be completed within the integrated sample preparation cartridge 200. The third sample port 53 and the fourth sample port 54 may be connected to waste bottles to collect the flow-through from the sample preparation device 100.

The integrated sample preparation cartridge 200 can be configured to be compatible with fluidic control systems, such as the Flow Pro Fluidic Handling System (Global FIA, Fox Island, Wash.). In one embodiment, the first sample outlet 53 and the second sample outlet 54 are fitted with Luer-activated valves 59. The Luer-activated valves 59 are normally closed valves that may be opened only upon insertion of a luer-type fitting. The Luer-activated valves 59 allow easy insertion into the fluidic control system and prevent leaking of sample from the sample preparation cartridge 200 after the sample preparation cartridge 200 is removed from the fluidic control system. In one embodiment, the integrated sample preparation cartridge 200 is designed to be plugged into a fluidic control system without the need for tightening screws or adjusting bolts.

A person of ordinary skill in the art understands that the general layout of the integrated sample preparation cartridge 200 allows for other sample introduction and elution withdrawal strategies. In one embodiment, the sample preparation cartridge 200 is connected to a fluidic control system. The sample preparation device 100 is inserted into the first sample port 51. A sample is introduced into the integrated sample preparation cartridge 200 through the second sample port 52, which is sealed off after the introduction of the sample. A chaotrophe, such as guanidine, is introduced into the integrated sample preparation cartridge 200 through the fourth sample port 54 by the fluidic control system and mixed with the sample within the integrated sample preparation cartridge 200. The sample/chaotrophe mixture is then pushed into the sample preparation device 100 from the second opening 16 of the sample preparation device 100, passing the filter 20 and entering the section of the housing 10 that is above the sample filter 20. The sample/chaotrophe mixture is then withdrawn from the integrated sample preparation cartridge 200 through the fourth sample port 54 and discarded as waste. A washing buffer is introduced into the integrated sample preparation cartridge 200 through the third sample port 53 by the fluidic control system. Similar to the movement of the sample/chaotrophe mixture, the washing buffer is forced into and then withdrawn from the sample preparation device 100, passing the filter 20 twice during the process. The washing step may be repeated several times. Finally, an eluting buffer is introduced into the sample preparation device 100 through the second opening 16, eluting the bound nucleic acids into the section of the housing 10 that is above the sample filter 20, from where the eluant is removed for further analysis.

In another embodiment, the sample is introduced through the first opening 14 of the sample preparation device 100 which is attached to the first sample port 51, and the eluant is removed from the second sample port 52. In another embodiment, the sample is introduced through the first opening 14 of sample preparation device 100, which is attached to the first sample port 51, and the eluant is removed from the first opening 14 of sample preparation device 100. In another embodiment, the sample is introduced onto the sample preparation device 100, which is attached to the first sample port 51, through the second sample port 52, and the eluant is removed from the second sample port 52. In another embodiment, the sample is pre-loaded into the sample preparation device 100 before the sample preparation device 100 is inserted into the first sample port 51 of the integrated sample preparation cartridge 200. After the washing and eluting steps, the eluant is removed from the second sample port 52. In yet another embodiment, the sample is pre-loaded into the sample preparation device 100 before the sample preparation device 100 is inserted into the first sample port 51 of the integrated sample preparation cartridge 200. After the washing step, the analyte bound on the sample filter 20 are eluted into the sample preparation device 100, which is then removed from the first sample port 51 with the purified analyte in the elution buffer within the space between the sample filter 20 and the aerosol filter 40.

The integrated sample preparation cartridge 200 is easy to use. First, this device does not require centrifugation and thus eliminates the complexity associated with transferring samples from tubes to spin columns as well as simplifies the instrumentation required. Additionally a self-sealing entry port for a pipettor allows easy introduction of the sample without the risk of opening caps, which are often a cause of contamination. Additionally, the Luer-activated valves make cartridge insertion and removal simple and easy without the risk of losing sample due to leakage after the process is complete.

In addition, the vertical orientation of the sample preparation device 100 forces bubbles to rise to the top of the device from the sample filter 20, which improves fluidic control and enhances analyte binding and elution. Additionally, the small pores of the sample filter 20 reduces large air boluses into small bubbles which migrate to the top of the liquid column inside the sample passage way 12, creating a vibrant mixing effect of the chaotrophe with the sample. It should be noted that the pipette tip configuration of the sample preparation device 100 allows bidirectional flow of the sample/washing/elution liquids through the sample filter 20, while most sample preparation approaches rely on flow in only one direction through the filter. The bidirectional flow feature not only allows the sample liquid to be taken into the sample preparation device 100 and eluted out of the sample preparation device 100 from the same opening (e.g., the second opening 16), but also permits a user to pipette a sample up and down for a number of cycles, thus providing the capability to process sample volumes larger than that of the sample preparation device 100.

In one embodiment, the channels 55, 56 and 57 are designed to have the shortest possible length to reduce unwanted biomolecular (nucleic acid) adsorption to the interior surfaces of the integrated sample preparation cartridge 200. The channels may also be surface coated to reduce unwanted biomolecule adsorption. In one embodiment, the channels 55, 56 and 57 have diameters in the range of 0.1-5 mm to reduce the surface-to-volume ratios and therefore reduce unwanted nucleic acid adsorption.

After the removal of the eluant, the integrated sample preparation cartridge 200 is removed from the Flow Control Station and discarded.

The base 50 of the integrated sample preparation cartridge 200 can be made of any material that is resistant to the chemicals commonly used in the sample solubilization/washing/eluting process. In one embodiment, the base 50 is made of a transparent material. Examples of the base 50 materials include, but are not limited to, polycarbonate and polypropylene.

The fluidic control system can be any fluidic control system that is capable of providing the desired flow rate in the integrated sample preparation cartridge 200. In one embodiment, the fluidic control system is the Flow Pro Fluidic Handling System by Global FIA (Fox Island, Wash.).

EXAMPLES

Example 1

Purification of Nucleic Acids from Blood Sample Containing *Bacillus anthracis* Using 2.0 ml Rainin Filtered Pipette Tip and 3 mm Glass Frit In this experiment, nucleic acids were purified from a blood sample containing *Bacillus anthracis* using a 2.0 ml Rainin filtered pipette tip and a 3 mm glass frit with the following protocol:

1. Label one 15 ml conical tube as: Flow Through, and four 1.5 ml centrifuge tubes as: Ethanol 1, Ethanol 2, Ethanol 3, and Eluant.
2. Mix 360 µl of blood with 40 µl of *Bacillus anthracis* ($10^5$ colony forming unit (cfu)/ml in water) in the Flow Through tube (final concentration $10^4$ cfu/ml).
3. Add 1120 µl of Qiagen AL Lysis Buffer to the mixture.
4. Add 80 µl of Proteinase K (20 mg/ml).
5. Add 400 µl of lysozyme, vortex and spin down.
6. Incubate the sample mixture at 55° C. for 1 hour.
7. Add 2000 µl of 96-100% ethanol to the Flow Through Tube. Vortex and pulse spin down the mixture.
8. Aliquot 100 µl of elution buffer (10 mM Tris, pH 8.0) into the Eluant tube. Place the tube on the heat block set at 70° C. (Elution buffer must be heated at 70° C. for at least 5 minutes. Keep the buffer on the heat block until step 13.)
9. Aliquot 1 ml of 70% Ethanol into each of the three Ethanol tubes.
10. Pipette sample mixture into the Flow Through tube using frit tip (medium porosity) with a Rainin Electronic Pipettor. Pipette for 5 cycles (cycle=aspirate+dispense).
11. Wash the bound nucleic acids by pipetting the 70% EtOH in Ethanol 1 tube for 10 cycles using a Rainin electronic Pipettor. Repeat the wash with the 70% EtOH in Ethanol 2 tube and Ethanol 3 tube (three washes total).
12. Purge the EtOH from the frit tip by pipetting air for 20 cycles. Wipe the outside of the tip and tap the tip gently if a noticeable amount of ethanol is left.
13. Elute the nucleic acids on the frit by pipetting the 70° C. elution buffer of step 8 for 10 cycles. The buffer may start to bubble but continue pipetting and spin down the microcentrifuge tube once complete. Make sure all the buffer has been purged from the tip.
14. Collect the eluant and discard the frit tip
15. Quantitating the eluted nucleic acids with real time PCR.

As shown in FIG. 3, nucleic acids from *Bacillus anthracis* are detected in the eluant.

Example 2

Purification of Nucleic Acids from *Streptococcus pyogenes* Using 2.0 ml Rainin Filtered Pipette Tip and 2 mm Glass Frit In this experiment, nucleic acids were purified from *Streptococcus pyogenes* suspensions of various concentrations using a 2.0 ml Rainin filtered pipette tip and a 2 mm glass frit with the following protocol:

1. Label three 1.5 ml centrifuge tubes as: Sample+Guanidine, Ethanol, and Eluant.
2. Lyse by vortexing with glass beads.
3. Mix 500 µl of *Streptococcus pyogenes* sample with 500 µl of 6M guanidine, pH 6.5, by vortexing. An aliquot of unprocessed (i.e., the pre-guanidine) *Streptococcus pyogenes* were also saved as a control for real-time PCR analysis in step 10.
4. Aliquot 100 µl elution buffer (1 mM NaOH) into the eluant tube. Pipette the sample/guanidine mixture with a frit tip (medium porosity) and a Rainin Electronic Pipettor. Pipette for 5 cycles (cycle=aspirate+dispense).
5. Pipette 1 ml 70% EtOH to wash bound nucleic acids using the Rainin electronic Pipettor for 5 cycles.
6. Pass air through the frit tip to purge EtOH using the electronic pipettor. Repeat pipetting for 20 cycles to remove traces of EtOH. Tap the frit tip gently if a noticeable amount of ethanol is left. Remove the EtOH on the outside of the tip with Kimwipe®.
7. Elute the nucleic acids from the frit with the 70° C. elution buffer from step 4 by pipetting for 10 cycles. Make sure all the elution buffer has been purged from the tip.
8. Collect the eluant and discard the frit tip
9. Quantitating the eluted nucleic acids with real time PCR.

As shown in FIG. 4, *Streptococcus pyogenes* nucleic acids are detected in samples prepared by the frit tip.

Example 3

Purification of Nucleic Acids from Nasopharyngeal Sample Containing *Bacillus anthracis* Using 2.0 ml Rainin Filtered Pipette Tip and 2 mm Glass Frit In this experiment, nucleic acids were purified from nasopharyngeal sample containing *Bacillus anthracis* using a 2.0 ml Rainin filtered pipette tip and a 2 mm frit with the following protocol:

1. Label three 1.5 ml centrifuge tubes as: Sample+Guanidine, Ethanol, and Eluant.
2. Prepare nasopharyngeal sample by mixing 450 µl of nasopharyngeal with 50 µl of *Bacillus anthracis* ($10^5$ colony forming unit (cfu)/ml in water) in the Sample+Guanidine tube (final concentration $10^4$ cfu/ml). Save an aliquot of the nasopharyngeal sample as control in the real-time PCR analysis of Step 11.
3. Add 500 µl of 6M guanidine, pH 6.5, into the Sample+Guanidine tube and vortex.
4. Aliquot 100 µl of elution buffer (10 mM Tris, pH 8.0) into the Eluant tube. Place the tube on the heat block set at 70° C. (elution buffer must heat at 70° C. for at least 5 minutes). Keep the tube on the heat block until step 9.

5. Pipette the sample/guanidine mixture using a frit tip (medium porosity) with a Rainin Electronic Pipettor. Pipette for 5 cycles (cycle=aspirate+dispense).
6. Pipette 1 ml 70% EtOH to wash bound nucleic acids using the Rainin electronic Pipettor.
7. Pass air through the frit tip to purge EtOH using the electronic pipettor. Repeat pipetting for 20 cycles to remove traces of EtOH. Tap the frit tip gently if a noticeable amount of ethanol is left. Remove the EtOH on the outside of the tip with Kimwipe®
8. Elute the nucleic acids from the frit with the 70° C. elution buffer from step 4 by pipetting for 10 cycles. Make sure all the elution buffer has been purged from the tip.
9. Collect the eluant and discard the frit tip
10. Quantitating the eluted nucleic acids with real time PCR.

Figure 5:
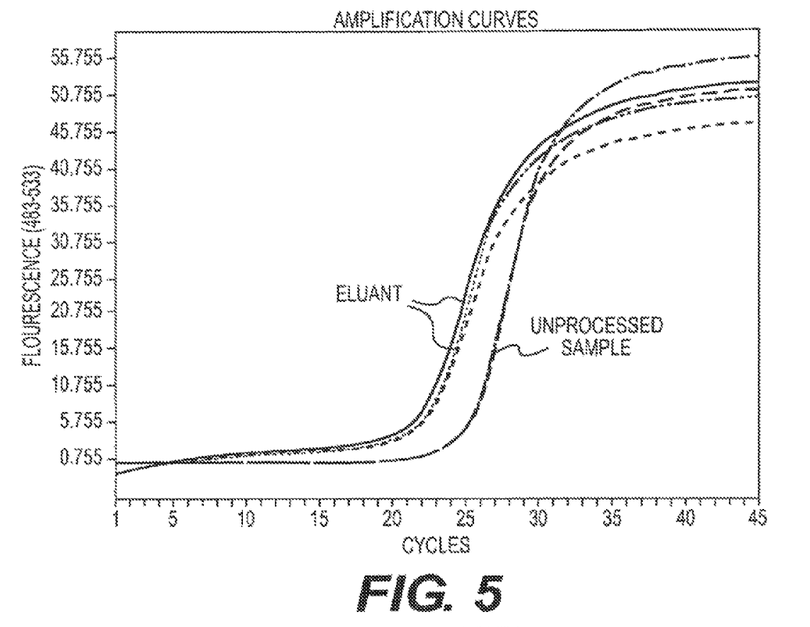

As shown in FIG. 5, nucleic acids from *Bacillus anthracis* are detected in the eluant.

Example 4

Purification of Nucleic Acids from Blood Sample Containing Venezuela Equine Encephalitis virus Using 1.2 ml Gilson Filtered Pipette Tip and 5 mm Glass Frit In this experiment, nucleic acids were purified from blood sample containing Venezuela Equine Encephalitis virus using a 2.0 ml Rainin filtered pipette tip and a 5 mm glass frit with the following protocol:
1. Label six 1.5 ml centrifuge tubes as: Flow Through, Ethanol 1, Ethanol 2, Ethanol 3, Eluant 1 and Eluant 2.
2. Mix 90 μl of blood with 10 μl of Venezuela Equine Encephalitis virus ($10^5$ plaque forming unit (pfu)/ml in water) in the Flow Through tube (final concentration $10^4$ pfu/ml).
3. Add 280 μl of Qiagen AL Lysis Buffer to the mixture.
4. Add 40 μl of Proteinase K (20 mg/ml).
5. Add 100 μl of lysozyme, vortex and spin down.
6. Incubate the sample mixture at 55° C. for 1 hour.
7. Add 500 μl of 96-100% ethanol to the Flow Through Tube. Vortex and pulse spin down the mixture.
8. Aliquot 100 μl of elution buffer (10 mM Tris, pH 8.0) into the Eluant tubes. Place the tubes on the heat block set at 70° C. (Elution buffer must be heated at 70° C. for at least 5 minutes. Keep the tubes on the heat block until step 13.)
9. Aliquot 1 ml of 70% Ethanol into each of the three Ethanol tubes.
10. Pipette sample mixture into the Flow Through tube using frit tip (medium porosity) with a Gilson Electronic Pipettor. Pipette for 5 cycles (cycle=aspirate+dispense). Wash the bound nucleic acids by pipetting the 70% EtOH in Ethanol 1 tube for 10 cycles using the electronic Pipettor. Repeat the wash with the 70% EtOH in Ethanol 2 tube and Ethanol 3 tube (three washes total). Purge the EtOH from the frit tip by pipetting air for 20 cycles. Wipe the outside of the tip and tap the tip gently if a noticeable amount of ethanol is left.
11. Elute the nucleic acids on the frit by pipetting the 70° C. elution buffer of step 8 for 10 cycles. Remove the elution buffer from the heat block once the cycles are completed. Make sure all the buffer has been purged from the tip.
12. Collect the eluant in Eluant 1 tube.
13. Repeat the step 13 with the same frit tip, collect the eluant in Eluant 2 tube, and discard the frit tip
14. Quantitating the eluted nucleic acids with real time PCR.

Figure 6:
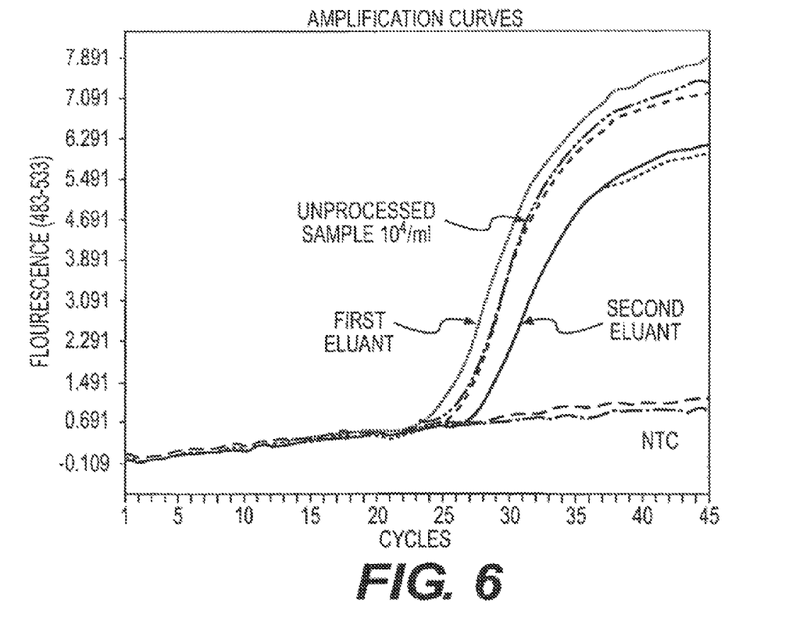

As shown in FIG. 6, nucleic acids from Venezuela Equine Encephalitis virus are detected in both the first and second eluant. The first eluant, however, contains nucleic acids of Venezuela Equine Encephalitis at a much higher concentration.

Example 5

Figure 7:
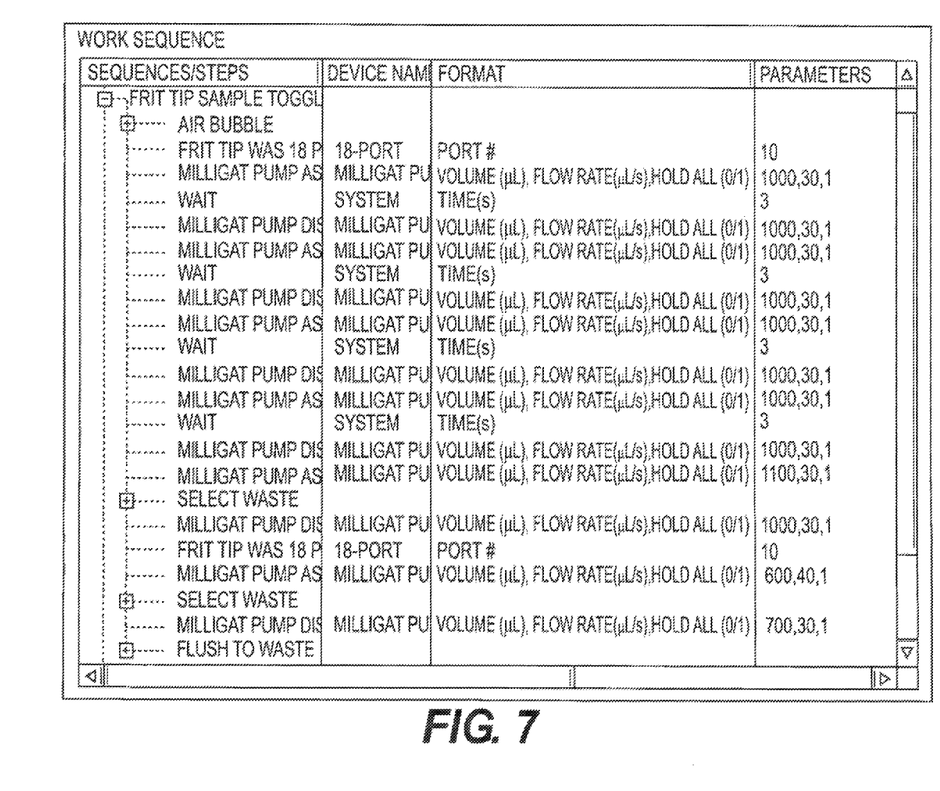

Automatic Sample Preparation Using Fluidic Control System and the Integrated Sample Preparation System A prototype of the integrated sample preparation device shown in FIG. 2A was connected to a Flow Pro Fluidic Handling System (Global FIA, Fox Island, Wash.). Nucleic acids were purified from Yersinia pestis suspension with the following protocol:
1. Label two 1.5 ml centrifuge tubes as: Sample and Eluant.
2. Aliquot 150 μl of 1 mM NaOH into a tube designated "Elution Buffer" which is located on the Global FIA system.
3. Aliquot 500 μl 70% EtOH into a Wash tube which is located on the Global FIA system.
4. Mix the 500 μl of Yersinia pestis suspension ($10^4$ cfu/ml in water) with 500 μl of 6M guanidine, pH 6.5, in the "sample" tube (step 1) and vortex. Save some un-mixed sample for analysis later.
5. Pipette the sample/guanidine mixture into frit tip (medium porosity) with a Rainin Electronic Pipettor.
6. Place the frit tip (with sample inside) onto the Sample Prep Cartridge located on the Global FIA device.
7. Perform the "Frit Tip Sample Toggle" sequence (FIG. 7) using the FloLV Software.
8. Perform the "Frit Tip EtOH Wash" sequence using the FloLV Software.
9. Perform the "Frit Tip EtOH Dry" sequence using the FloLV Software.
10. Perform the "Frit Tip Elution" sequence using the FloLV Software.
11. Once the sequence is completed, remove the frit tip from the Global FIA system, attach the frit tip to a Rainin Electronic Pipettor and dispense the eluant into the 1.5 ml centrifuge tube labeled "Eluant".
11. Discard the frit tip.
12. Quantitating the eluted nucleic acids with real time PCR.

Figure 8:
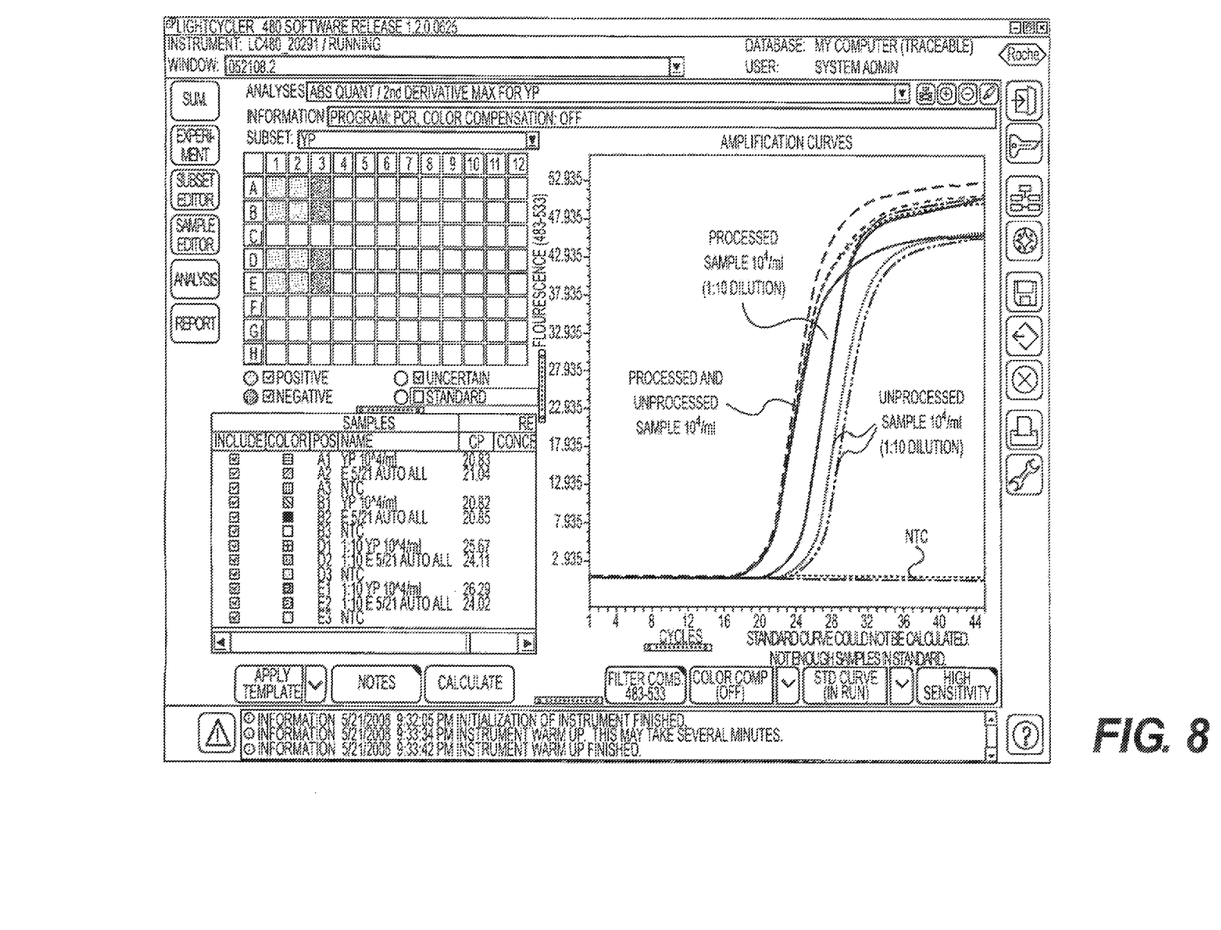

As shown in FIG. 8, nucleic acids from Yersinia pestis are detected in the eluant.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

The invention claimed is:
1. A method for purifying an analyte from a liquid sample, comprising:
    placing said liquid sample in a container;
    withdrawing at least a portion of said liquid sample into a sample preparation device comprising:
        a housing defining a passage way between a first opening and a second opening; and a filter occupying a section of said passage way, said filter comprising a material that specifically binds to said analyte,
wherein said portion of liquid sample is drawn into said housing via the first opening and passing through said filter, wherein said filter comprises a glass frit, and wherein said analyte is a nucleic acid that binds to said glass frit while passing through said filter;
expelling said portion of liquid sample from said sample preparation device via the first opening, wherein said portion of liquid sample passes through said filter a second time while exiting said sample preparation device; and
eluting said analyte from said filter by withdrawing an eluting buffer into said sample preparation device via the first opening and expelling said eluting buffer from said sample preparation device via the first opening, wherein said eluting buffer passes through said filter while entering and exiting said sample preparation device.

2. The method of claim 1, wherein said sample withdrawing and sample expelling steps are repeated until all said liquid sample passes through said filter at least once.

3. The method of claim 1, wherein said sample preparation device has the configuration of a pipette tip.

4. The method of claim 1, wherein said withdrawing, expelling and eluting steps are controlled by an electronic pipettor.

5. The method of claim 1, wherein said withdrawing, expelling and eluting steps are controlled by an robotic pipetting station.

6. The method of claim 1, wherein said glass frit has a pore size between about 2 microns and about 220 microns.

7. The method of claim 1, wherein said glass frit has a thickness between about 2 mm and about 5 mm.

8. The method of claim 1, wherein said sample preparation device comprises two or more filters of different porosity, wherein said two or more filters bind specifically to nucleic acids.

9. The method of claim 1, further comprising:
washing said filter by withdrawing a washing buffer into said sample preparation device via the first opening and expelling said washing buffer from said sample preparation device via the first opening, wherein said washing buffer passes through said filter while entering and exiting said sample preparation device.

10. The method of claim 9 wherein said washing step is repeated two or more times.

11. A method for purifying an analyte from a sample, comprising:
passing said sample through a sample preparation device comprising:
a housing defining a passage way between a first opening and a second opening; and
a sample filter occupying a section of said passage way, wherein said sample filter comprises a glass frit that specifically binds to said analyte and said sample passes through said sample filter while passing through said sample preparation device; and
eluting analyte bound to said sample filter with an eluting solution,
wherein said sample and said eluting solution enter and exit said housing through the same opening.

12. The method of claim 11, wherein said sample preparation device is attached to a cartridge base comprising a first port configured to receive said sample preparation device and a second port configured to receive a liquid delivery device.

13. The method of claim 11, further comprising:
washing said sample filter with a washing solution, wherein said washing solution enter and exit said housing through the same opening.

14. The method of claim 11, wherein said sample preparation device comprises two or more sample filters of different porosity, wherein said two or more filters bind specifically to nucleic acids.

15. The method of claim 11, wherein said analyte is a nucleic acid.

16. The method of claim 15, wherein said porous glass fit has a pore size between about 2 microns and about 220 microns.

17. The method of claim 15, wherein said porous glass frit has a thickness between about 2 mm and about 5 mm.

* * * * *